(12) United States Patent
Calvin et al.

(10) Patent No.: US 7,881,518 B2
(45) Date of Patent: *Feb. 1, 2011

(54) METHODS FOR ALTERING ONE OR MORE PARAMETERS OF A MEASUREMENT SYSTEM

(75) Inventors: Edward Calvin, Houston, TX (US); Wayne D. Roth, Leander, TX (US)

(73) Assignee: Luminex Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/421,186

(22) Filed: Apr. 9, 2009

(65) Prior Publication Data

US 2009/0237658 A1 Sep. 24, 2009

Related U.S. Application Data

(63) Continuation of application No. 11/031,905, filed on Jan. 7, 2005, now Pat. No. 7,551,763.

(60) Provisional application No. 60/536,466, filed on Jan. 14, 2004.

(51) Int. Cl.
  *G06K 9/00* (2006.01)
  *C12Q 1/68* (2006.01)
(52) U.S. Cl. .............. 382/133; 382/224; 435/6
(58) Field of Classification Search ............ 382/100, 382/106, 107, 128, 129, 130, 131, 132, 133, 382/134, 162, 168, 181, 191, 199, 203, 209, 382/224, 232, 254, 255, 274, 287–291, 305, 382/318; 702/19; 435/6, 7.24; 506/3

See application file for complete search history.

(56) References Cited

U.S. PATENT DOCUMENTS

| | | | |
|---|---|---|---|
| 4,661,913 A * | 4/1987 | Wu et al. | .............. 702/19 |
| 5,736,330 A | 4/1998 | Fulton | |
| 5,739,000 A * | 4/1998 | Bierre et al. | .............. 435/7.24 |
| 5,981,180 A * | 11/1999 | Chandler et al. | .............. 435/6 |
| 6,046,807 A | 4/2000 | Chandler | |
| 6,057,107 A | 5/2000 | Fulton | |
| 6,139,800 A | 10/2000 | Chandler | |
| 6,268,222 B1 | 7/2001 | Chandler et al. | |

(Continued)

FOREIGN PATENT DOCUMENTS

WO 97/14028 4/1997

OTHER PUBLICATIONS

International Search Report, PCT/US2005/000509, mailed May 6, 2005.

*Primary Examiner*—Seyed Azarian
(74) *Attorney, Agent, or Firm*—Kevin L. Daffer; Mollie E. Lettang; Daffer McDaniel, LLP

(57) ABSTRACT

Methods for altering one or more parameters of a measurement system are provided. One method includes analyzing a sample using the system to generate values from classification channels of the system for a population of particles in the sample. The method also includes identifying a region in a classification space in which the values for the populations are located. In addition, the method includes determining an optimized classification region for the population using one or more properties of the region. The optimized classification region contains a predetermined percentage of the values for the population. The optimized classification region is used for classification of particles in additional samples.

20 Claims, 6 Drawing Sheets

U.S. PATENT DOCUMENTS

| | | |
|---|---|---|
| 6,366,354 B1 | 4/2002 | Chandler |
| 6,411,904 B1 | 6/2002 | Chandler |
| 6,449,562 B1 * | 9/2002 | Chandler et al. .............. 702/19 |
| 6,514,295 B1 | 2/2003 | Chandler et al. |
| 6,524,793 B1 * | 2/2003 | Chandler et al. ............... 435/6 |
| 6,528,165 B2 | 3/2003 | Chandler |
| 6,586,193 B2 * | 7/2003 | Yguerabide et al. ............ 506/3 |
| 2005/0073686 A1 | 4/2005 | Roth et al. |

* cited by examiner

METHODS FOR ALTERING ONE OR MORE PARAMETERS OF A MEASUREMENT SYSTEM

PRIORITY CLAIM

The present application is a continuation from prior U.S. application Ser. No. 11/031,905 filed Jan. 7, 2005 which claims priority to U.S. Provisional Application No. 60/536,466 filed Jan. 14, 2004.

BACKGROUND OF THE INVENTION

1. Field of the Invention

This invention generally relates to methods for altering one or more parameters of a measurement system. Certain embodiments relate to methods and systems for optimizing one or more parameters of a measurement system for classifying particles of a population.

2. Description of the Related Art

The following descriptions and examples are not admitted to be prior art by virtue of their inclusion within this section.

Generally, flow cytometers provide measurements of fluorescence intensity of laser excited polystyrene beads as they pass linearly through a flow chamber. In some systems, there are four measurements that are performed: the level of light scattered by a bead at 90 degrees to the excitation source, two measurements of fluorescence used to determine the bead "identity" or "classification," and a third fluorescence measurement typically used to detect and/or quantify a surface chemical reaction of interest. Each of the three fluorescent measurements is made at a different wavelength. These and any other fluorescent measurements are performed by different "channels" of the system (e.g., reporter channels, classification channels), which include a detector and possibly other components (e.g., optical components, electronic components, etc.) coupled to the detector.

In one example, the fluorescence measurement of the chemical reaction is quantified by optically projecting an image of the bead as it passes through the illumination zone of the excitation laser on the photosensitive area of a photomultiplier tube (PMT). The output of the PMT is a current pulse, which is then conditioned by analog electronics and digitized by an analog to digital (A/D) converter. The resultant digital values obtained from the A/D converter may be further conditioned in the digital domain by a digital signal processing (DSP) algorithm. The end product per bead is a single integer value, which is generally proportional to the chemical reaction on the surface of the bead.

Each flow cytometer based system such as the Luminex 100 system, which is manufactured by Luminex Corp., Austin, Tex., displays results of particle measurements (e.g., the 100-region LabMAP) in a slightly different way than a "typical" flow cytometer instrument. These differences in the displays are a result of the accumulated tolerance for many of the components of the system such as the diode laser, the photodiodes, the optical filters, and the electronics used to process the data. In particular, particles are classified by comparing values generated during analysis of the particles to regions located in a classification space (e.g., the Map). Particles having values that are located within a region in the classification space are assigned the classification corresponding to this region. Therefore, in order to account for the accumulated tolerance of the system described above, the size of the regions in the classification space that are used to classify different populations are made larger than necessary to contain the values of the different populations.

One result of using these larger than necessary classification regions is inconsistent classification of particle populations between one system and another. For instance, one system might be able to classify 95% of a particle population as belonging to a particular region, and 0.5% of that population would typically be misclassified in another region, whereas a different system might correctly classify 98% of this particle population and misclassify a smaller percentage of the population. Therefore, using a larger than necessary classification region results in poor system-to-system matching. System-to-system matching, however, may be desirable, for example, when multiple measurement systems are used in a single facility or organization to perform assays on biological samples. In this manner, results obtained using one measurement system may be directly compared to results obtained using a different measurement system.

Obviously, one way to reduce the size of the classification regions is to reduce the accumulated tolerance of the system. One way to reduce the accumulated tolerance of the system is to manufacture the system using components that have extremely narrow tolerances. However, using such components places a significant burden on manufacturing personnel in sourcing these components. In addition, rigorous assembly efforts can be used to try to compensate for tight tolerances. However, like the extremely narrow tolerance components, using rigorous assembly efforts increases the complexity and difficulty of manufacturing. Therefore, currently available methods for reducing the size of the classification regions increase system manufacturing time, decrease manufacturing throughput, and increase overall system cost.

Accordingly, it would be desirable to reduce the size of the classification regions such that the system can classify particles with greater system accuracy and greater system-to-system uniformity without complicating the manufacturing process, increasing the manufacturing time, decreasing manufacturing throughput, and increasing overall system cost.

SUMMARY OF THE INVENTION

The following description of various embodiments of methods for altering one or more parameters of a measurement system is not to be construed in any way as limiting the subject matter of the appended claims.

One embodiment of the invention relates to a method for altering one or more parameters of a measurement system. The method includes analyzing a sample using the system to generate values from classification channels of the system for a population of particles in the sample. The method also includes identifying a region in a classification space in which the values for the population are located. In addition, the method includes determining an optimized classification region for the population using one or more properties of the region. The optimized classification region contains a predetermined percentage of the values for the population. The optimized classification region can be used for classification of particles in additional samples.

In some embodiments, the optimized classification region has one or more properties that are different from the one or more properties of the region. The one or more properties include size, shape, position, or some combination thereof. In one embodiment, the method includes calibrating the system prior to the analyzing step. The sample may include, in some embodiments, a Map Calibration Reagent. The values may be expressed in linear units or logarithmic units.

In an embodiment, the one or more properties of the region include an average, mean, peak, or median of the values in the region and a standard deviation of the values in the region. In another embodiment, the optimized classification region centers on a median of the values in the region plus a number of standard deviations away from the median. In an additional embodiment, the optimized classification region is defined by a predetermined sized boundary surrounding a median of the values for the population. The size of the optimized classification region is, in some embodiments, a minimum size that contains the predetermined percentage of the values for the population.

In one embodiment, the values from the classification channels include fluorescence values. In a different embodiment, the values from the classification channels include light scatter intensity values. In other embodiments, the values from the classification channels include volume measurements of the particles. In another embodiment, the values may include some combination of the different values (e.g., fluorescence values and light scatter intensity values, etc.).

The sample may, in some embodiments, include one or more additional populations of particles. In one such embodiment, the method is performed for the one or more additional populations. In this manner, an optimized classification region may be determined for each of the one or more additional populations. In another such embodiment, the method may include interpolating an optimized classification region for another population of particles that was not included in the sample using the optimized classification regions of the population and the one or more additional populations.

In one embodiment, the one or more properties of the region may include, as described above, an average, mean, peak, or median of the values for the population and a standard deviation of the values for the population. In one such embodiment, the method may include comparing at least one of the one or more properties to a predetermined range for the at least one of the one or more properties. Such an embodiment may include assessing performance of the system based on results of the comparing step. If the at least one of the one or more properties of the region is outside of the predetermined range, another such embodiment of the method may include determining if one or more corrective steps should be performed on the system.

In another embodiment, the method may include comparing one or more properties of the optimized classification region to the one or more properties of the region. In one such embodiment, the one or more properties of the optimized classification region and the region include size, centroid position, slope of a best-fit line to the values inside the region or the optimized classification region, offset of the best-fit line, or some combination thereof. In another such embodiment, if the results of this comparing step exceed a predetermined limit, the method may include determining if the system is malfunctioning.

In a further embodiment, the optimized classification region includes a portion of the classification space, and a probability that the particles will have values located in the portion of the classification space is greater than a predetermined probability. In another embodiment, the optimized classification region excludes a portion of the classification space, and a probability that the particles will have values located in the portion of the classification space is less than a predetermined probability. Each of the embodiments of the method described above may include any other step(s) described herein.

Another embodiment relates to a different method for altering one or more parameters of a measurement system. This method includes analyzing a sample using the system to generate values from classification channels of the system for two or more populations of particles in the sample. The method also includes identifying two or more regions in a classification space. In each of the two or more regions, the values for one of the two or more populations of particles are located. In addition, the method includes determining two or more optimized classification regions. Each of the two or more optimized classification regions corresponds to one of the two or more regions. The method further includes interpolating an optimized classification region for an additional population of particles not included in the sample using the two or more optimized classification regions. This embodiment may also include any other step(s) described herein.

An additional embodiment relates to a computer-implemented method for altering one or more parameters of a measurement system. The computer-implemented method includes identifying a region in a classification space in which values for a population of particles of a sample are located. The values include values generated by classification channels of the system during analysis of the sample. The computer-implemented method also includes determining an optimized classification region for the population using one or more properties of the region. The optimized classification region contains a predetermined percentage of the values for the population. The optimized classification region is used for classification of particles in additional samples. This embodiment of the computer-implemented method may include any other step(s) described herein.

BRIEF DESCRIPTION OF THE DRAWINGS

Other objects and advantages of the invention will become apparent upon reading the following detailed description and upon reference to the accompanying drawings in which.

Figure 1:
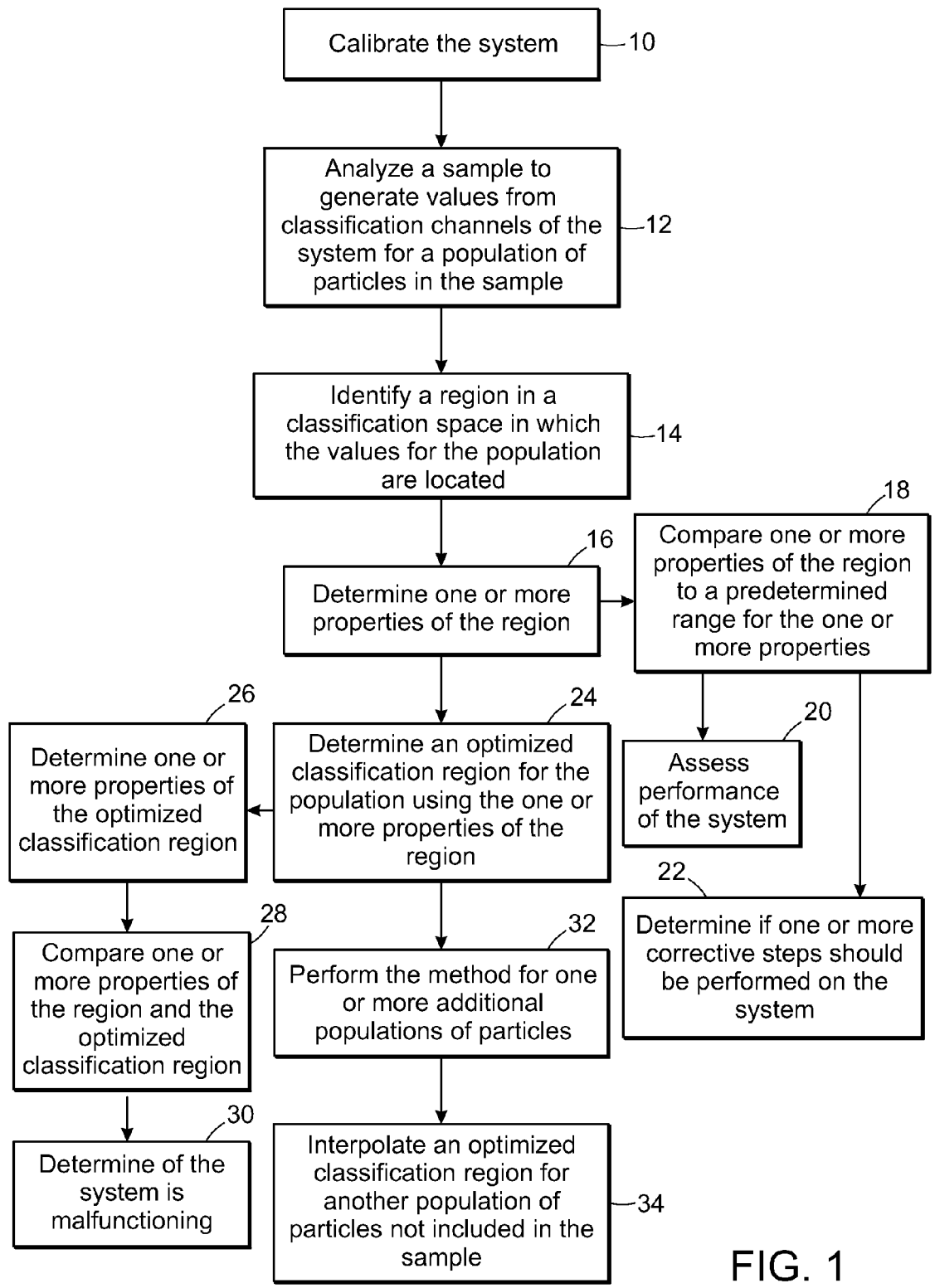
FIG. 1 is a flow chart illustrating one embodiment of a method for altering one or more parameters of a measurement system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The term "particles" is used herein to generally refer to particles, microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substrates or substances known in the art. The particles may serve as vehicles for molecular reactions. Examples of appropriate particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The measurement systems and methods described herein may be used with any of the particles described in these patents. In addition, particles for use in flow cytometry such as LabMAP microspheres, which may also be referred to as xMAP microspheres, may be obtained commercially from Luminex Corporation. The terms "particles" and "microspheres" are used interchangeably herein.

Methods are described herein for altering one or more parameters of a measurement system. In particular, the methods can be used to "tune" a measurement system such that the system can classify particles from a particular population with increased accuracy and such that the probability that the system will misclassify particles is decreased. As used herein, the term "classification" is generally defined as determining the identity of individual particles in a sample. The identity relates to the population to which individual particles belong. Such classification is of particular importance since often a sample will be analyzed with multiple, different populations of particles in a single experiment. For example, the different populations of particles typically have at least one different characteristic such as the type of substance coupled to the particles and/or the quantity of substances coupled to the particles such that the presence of different analytes within the sample can be detected and/or quantified in a single experiment. Therefore, to interpret the measurement results, the identify or classification of individual particles used in the experiment are determined such that other measurement values can be correlated to the properties of the individual particles.

Systems that can be configured to perform the methods described herein include, but are not limited to, the Luminex 100, the Luminex HTS, the Luminex 100E, and any further add-ons to this family of products that are available from Luminex Corporation. One general example of such systems is described further herein. In particular, the methods described herein can use the "Map method" of classifying particles in a flow cytometer-based system to alter one or more parameters of the flow cytometer-based system. However, it is to be understood that the methods described herein may be used to alter one or more parameters of any measurement system that is configured to determine the identity or classification of individual particles or other discrete substances. One example of such a measurement system is a fluorescent imaging system. In addition, the methods described herein are not limited to use in increasing the accuracy of particle classification. For example, the methods described herein may be equally applied to determining other classification parameters such as, but not limited to, the identity or quantity of a reaction product present on the particles. Furthermore, although various values are described herein that can be used with the methods, it is to be understood that the methods described herein may be used with any measurable parameter of particles that can be used to determine one or more characteristics of the particles.

As will be evident to one of ordinary skill in the art having the benefit of the description of the various embodiments provided herein, the methods described herein provide several advantages for analyzing values generated by a measurement system. In particular, the methods described herein provide greater system accuracy than is currently available without altering the physical parameters of the measurement system (e.g., without altering the accumulated tolerance of various components of the measurement system). Therefore, the methods described herein provide greater system accuracy without complicating the manufacturing process, increasing the manufacturing time, decreasing manufacturing throughput, and increasing overall system cost. In addition, since the methods described herein allow the classification space of a region corresponding to a population of particles to be reduced without decreasing the accuracy of the measurement system, the methods described herein provide greater system-to-system matching than is currently available. Since the system-to-system matching can be increased without altering the physical components of the measurement system, the methods described herein provide greater system-to-system matching without complicating the manufacturing process, increasing the manufacturing time, decreasing manufacturing throughput, and increasing overall system cost.

FIG. 1 illustrates an embodiment of a method for altering one or more parameters of a measurement system. It is noted that many of the steps shown in FIG. 1 are not essential to practice of the method. One or more steps may be omitted or added to the method illustrated in FIG. 1, and the method can still be practiced within the scope of this embodiment. In addition, it is to be noted that one or more steps of the method may be automated. In this manner, one or more steps of the method may be performed without supervision or instructions from a user of the measurement system. Alternatively, one or more steps of the method may be performed based on input from or interaction with a user such as an operator of the system, a field technician, or manufacturing personnel. Furthermore, one or more steps of the method or even all of the steps of the method may be computer-implemented. In this manner, one or more of the steps can be performed by a processor of the system, an algorithm or other program instructions that are operable to execute one or more of the steps on a processor such as those described herein or any other hardware or software known in the art.

As shown in step 10 of FIG. 1, the method may optionally include calibrating the measurement system. The method may include calibrating the system using normal or standard calibration reagents and procedures. One example of such a calibration procedure is the Map Calibration Procedure, which is commonly used on flow cytometer based measurement systems that are commercially available from Luminex Corporation. For example, a flow cytometer based measurement system identifies particles that pass through the system based on the measured intensity of two or more dyes internal or otherwise attached to the particles. This identification technique can also be used to identify a calibration microsphere that contains known quantities of fluorescent intensity in all channels (both reporter and classification). After the calibration microsphere measurement is performed, a fine correction factor can be applied to the reporter and/or classification channels for sample microsphere measurements. Additional examples of calibration techniques that may be used in step 10 are illustrated in U.S. patent Ser. No. 10/918,647 entitled "Methods for Controlling One or More Parameters of a Flow Cytometer Type Measurement System" filed Aug. 12, 2004 by Roth et al., which claims priority to U.S. Pat. No. 60/494, 824 entitled "Real Time System Calibration Methods" filed Aug. 13, 2003, by Roth, both of which are incorporated by reference as if fully set forth herein. Any other calibration technique known in the art can be used in this optional calibration step.

The method also includes analyzing a sample to generate values from classification channels of the system for a population of particles in the sample, as shown in step 12. In one embodiment, the sample may include a Map Calibration Reagent. A Map Calibration Reagent includes one or more populations of dyed microspheres from the product group that is commercially available as the 100-region LabMAP from Luminex Corporation, or possibly populations of microspheres that have similar intensities to those in the 100-region LabMAP, but are not part of the LabMAP. In addition, the sample may include any other appropriate sample known in the art such as a sample that includes at least one population of particles.

In one embodiment, the values from the classification channels include fluorescence values. In a different embodiment, the values from the classification channels include light scatter intensity values. In other embodiments, the values from the classification channels include volume measurements of the particles. In some embodiments, the values may include some combination of fluorescence values, light scatter intensity values, and volume measurements of the particles. Each of these different types of values may be expressed in linear units or logarithmic units.

In addition, the method includes identifying a region in a classification space in which the values for the population are located, as shown in step 14. The values may be organized in the classification space using any method known in the art such as a two-dimensional plot, with the values for the different classification channels along each of the two axes. Such a plot, in the context of flow cytometry-based instruments, is commonly referred to as a "map." Identifying the region in the classification space in which the values for the population are located may include defining a boundary around a cluster of values that contains values from as many of the particles in the population as possible, but excludes to the degree possible any particles that are not members of the population. The boundary, therefore, identifies the area in the classification space belonging to the region. Such a boundary may be generated by a user or by program instructions.

The method may optionally include determining one or more properties of the values of the population located within the region (hereafter referred to as properties of the region), as shown in step 16. The one or more properties of the region may include an average, mean, peak, or median of the values in the region and a standard deviation of the region. Such properties of the region may be determined using any method known in the art. The one or more properties of the region may be used to perform a number of functions. For example, in one embodiment, the method may include comparing at least one of the properties of the region to a predetermined range for the at least one property, as shown in step 18. The predetermined range may, in some embodiments, be representative of typical, acceptable, or expected performance of the system. In this manner, the method may optionally include assessing the performance of the system, as shown in step 20, based on results obtained in the comparing step. In other words, if one or more properties of the region are significantly different from the expected values for the properties, these significant differences may be detected by the comparing step and can be used to monitor system performance. In another example, if at least one of the properties is outside of the predetermined range, the method may include determining if one or more corrective steps should be performed on the system, as shown in optional step 22. The corrective step(s) may include, for example, calibration, maintenance, repair, troubleshooting, rebooting, etc.

The method includes determining an optimized classification region for the population using the one or more properties of the region, as shown in step 24. The optimized classification region contains a predetermined percentage of the values for the population. The predetermined percentage may, in some embodiments, reflect the desired accuracy of the measurement system (e.g., 98%, 95%, 90%, etc.). In another embodiment, the predetermined percentage may be determined based on the characteristics of the values in the region such as the distribution of the values within the region and other properties of the region described above. Since the optimized classification region will include only a predetermined percentage of the values in the region, the optimized classification region will usually, but not necessarily always, have a size in the classification region that is less than a size of the region in the classification space. In general, the optimized classification region will have one or more properties that are different from the one or more properties of the region. The one or more different properties may include size, shape, position, or some combination thereof. In one embodiment, the size of the optimized classification region may be a minimum size that contains the predetermined percentage of the values for the population. In some embodiments, the optimized classification region centers on a median of the values in the region plus a number of standard deviations (for example, two or three) away from the median. The median of the values may be determined empirically in one example. In another embodiment, the optimized classification region is defined by a predetermined sized boundary surrounding a median of the values for the population.

The optimized classification region can be used for classification of particles in additional samples. In particular, values of the classification channels generated for particles of other samples may be compared to this and possibly other optimized classification regions. If the values for a particle fall within one of the optimized classification regions, the particle is assigned the classification associated with that optimized classification region.

The optimized classification region provides significant advantages over other methods for classification such as greater system accuracy in classifying particles and greater system-to-system matching for particle classification. For example, the optimized classification region includes a portion of the classification space. The portion of the classification space within the optimized classification region may be determined as described above such that a probability that the particles will have values located in the portion of the classification space is greater than a predetermined probability. The predetermined probability may be determined based on a number of parameters such as statistical or other mathematical analysis of the expected results of particle measurements. The optimized classification region also excludes a portion of the classification space. The portion of the classification space excluded from the optimized classification region may be determined such that a probability that the particles will have values located in the excluded portion of the classification space is less than a predetermined probability. This predetermined probability will be different than the one described above, but both probabilities may be determined in the same manner.

In some embodiments, the method may include determining one or more properties of the optimized classification region, as shown in optional step 26. However, it is to be noted that the optimized classification region can be used for classification of particles in additional samples even if the one or more properties are not determined for the optimized classification region. The one or more properties of the optimized classification region may be used to perform a number of additional steps. For example, the method may include comparing one or more properties of the optimized classification region to the one or more properties of the region, as shown in optional step 28. The one or more properties of the optimized classification region and the region that are compared may include, but are not limited to, size, centroid position, slope of a best-fit line to the values inside the region or the optimized classification region, offset of the best-fit line, or some combination thereof. The results of the comparison step may also be used to perform one or more additional steps. In one such example, if the results of the comparing step exceed a predetermined limit, the method may include determining if the system is malfunctioning, as shown in optional step 30. The predetermined limit may be based on typical, acceptable, or expected properties for the regions. If it is determined that the system is malfunctioning, the method may include determining if one or more corrective steps such as those described above should be performed on the system.

The sample that is analyzed in step 12 may include one or more additional populations of particles. In one embodiment, the method may be performed for the one or more additional populations, as shown in optional step 32. In this manner, the method may include determining an optimized classification region for each of the one or more additional populations of particles. An optimized classification region may be determined for additional populations as described herein. It is to be noted that an optimized classification region may optionally not be determined for every population of particles in the sample. When two or more optimized classification regions are determined for a sample, the method may include interpolating an optimized classification region for another population of particles that was not included in the sample, as shown in optional step 34, using the two or more optimized classification regions. In addition, optimized classification regions for more than one population of particles not included in the sample may be determined in this manner.

Various steps illustrated in FIG. 1 may be combined to generate different embodiments of a method for altering one or more parameters of a measurement system. For example, one embodiment may include analyzing a sample using the system to generate values from classification channels of the system for two or more populations of particles in the sample, which may be performed as described with respect to step 12. In addition, this method includes identifying two or more regions in a classification space, which may be performed as described with respect to step 14. In each of the two or more regions, the values for one of the two or more populations of particles are located. The method also includes determining two or more optimized classification regions, which may be performed as described with respect to step 32. Each of the two or more optimized classification regions corresponds to one of the two or more regions. The method further includes interpolating an optimized classification region for an additional population of particles not included in the sample using the two or more optimized classification regions, which may be performed as described with respect to step 34. This embodiment of the method may include any other step(s) described herein.

In another example, an embodiment of a computer-implemented method for altering one or more parameters of a measurement system includes identifying a region in a classification space in which values for a population of particles of a sample are located, which may be performed as described with respect to step 14. The values include values generated by classification channels of the system during analysis of the system. This computer-implemented method also includes determining an optimized classification region for the population using one or more properties of the region, which may be performed as described with respect to step 24. As described further herein, the optimized classification region contains a predetermined percentage of the values for the population. The optimized classification region can be used for classification of particles in additional samples as described herein. This embodiment of a computer-implemented method may include any other step(s) described herein.

Figure 2:
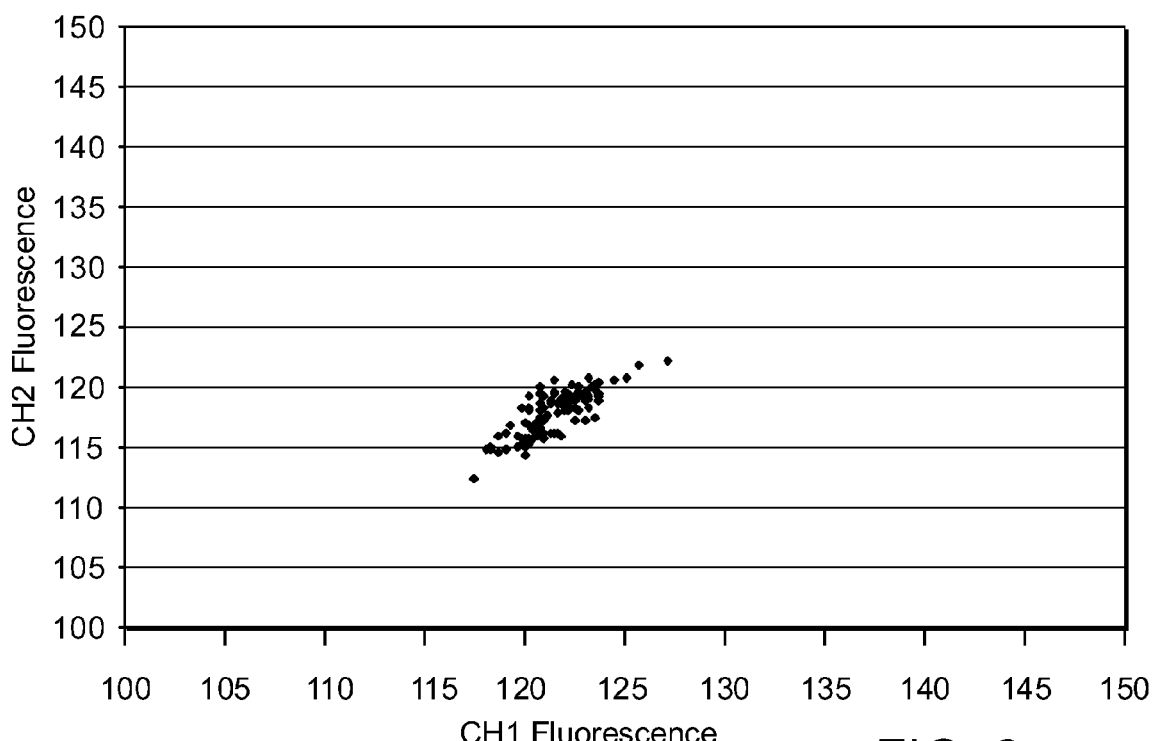
FIG. 2 is a plot illustrating flow cytometer data with 2-parameter fluorescence data for a single population of dyed particles.

One example of determining an optimized classification region may include the following steps, which may produce data as illustrated in FIGS. 2-6. It is noted that the data illustrated in FIGS. 2-6 is not meant to be exemplary or limiting examples of the methods described herein. Instead, this data is presented merely to enhance understanding of the methods described herein. FIG. 2 illustrates data obtained from a flow cytometer-like device in which two colors of fluorescence are used to identify the particles. The two colors of fluorescence were detected using two different classification channels, CH1 and CH2. A boundary is drawn around the cluster of data values that contains fluorescence data from as many of the particles in the population as possible, but excludes to the degree possible any particles that are not members of the population. The white region around the data points is bounded by a hand-drawn boundary, which adequately includes values for the population, but also includes extra space in which members of the population are unlikely to exhibit fluorescence. This region can be optimized by eliminating some of this extra space, so that in situations where the sample contains other fluorescent particles that are not members of this population, they can be easily discriminated by the optimized classification region.

Figure 3:
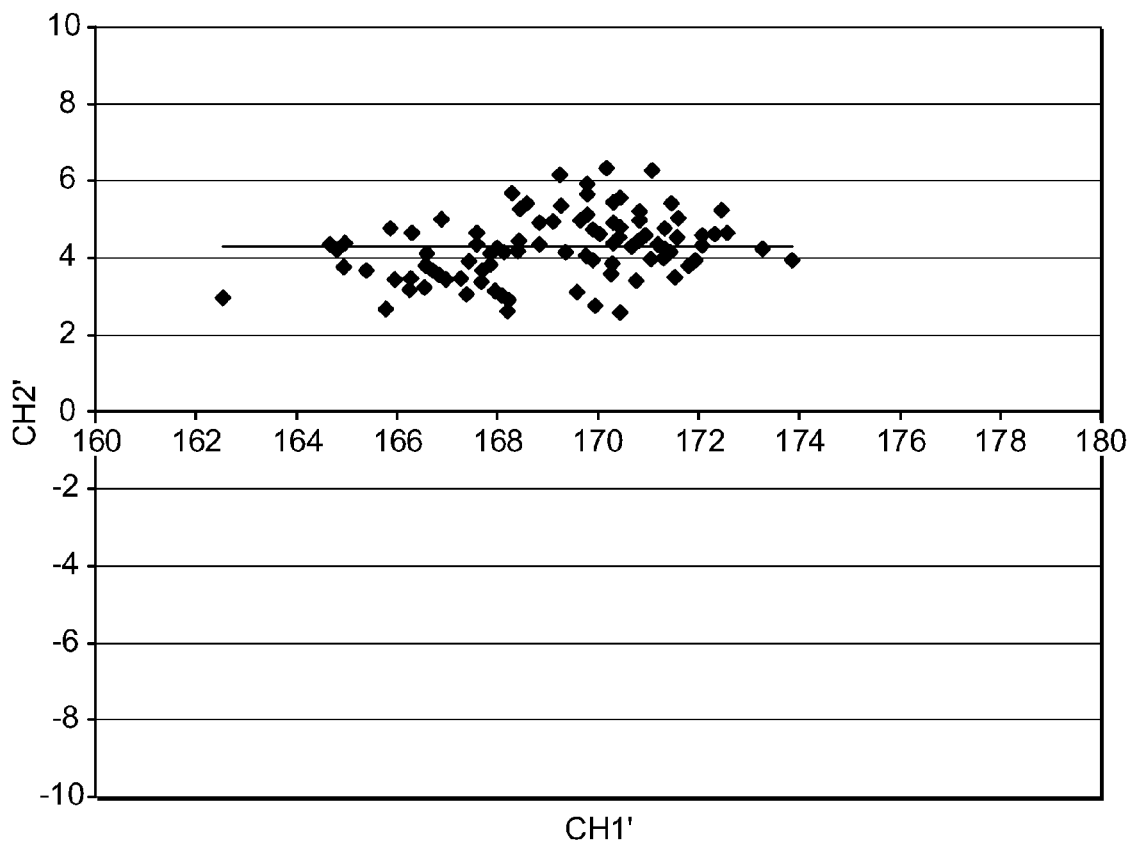
FIG. 3 is a plot illustrating the data of FIG. 2, which is rotated, with a best-fit line.

A linear regression is applied to the data shown in FIG. 2 to obtain the slope of the line that best fits this population. A "population" can then be defined as including any data within, for example, 25% of the median CH1 and CH2 values (i.e., a box bounded on the sides by Median_CH1+25%, Median_CH1−25%, and on the top and bottom by Median CH2+25%, Median_CH2−25%). After determining this slope, the entire data set is rotated so that the best-fit line is essentially horizontal (as shown in FIG. 3), with new coordinates of CH1' and CH2'. Using the rotated data set, a median and standard deviation is determined for the population in the CH1' and CH2' dimensions.

Figure 4:
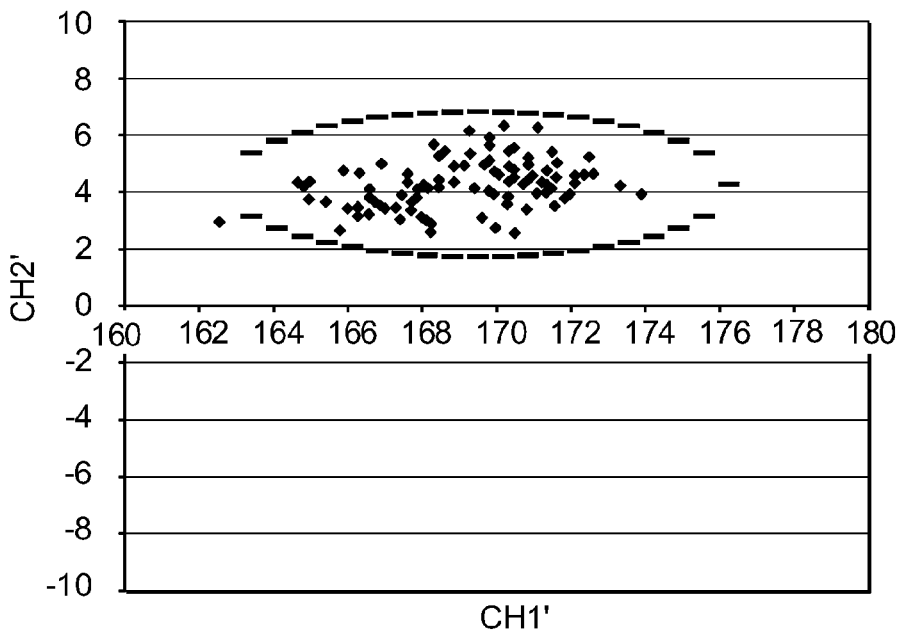
FIG. 4 is a plot illustrating a 3-standard deviation ellipse bounding the data of FIG. 3 in rotated coordinates.

As shown in FIG. 4, an ellipse is created having a center that is the median values in CH1' and CH2' and whose major and minor axes (although not necessarily in that order) are some constant C times the standard deviations in CH1' and CH2'. The constant is adjusted until the ellipse contains the desired percentage of particles in the population. In this example, giving C a value of 3 creates a boundary that encircles 98.9% of the population (as shown in FIG. 4).

Figure 5:
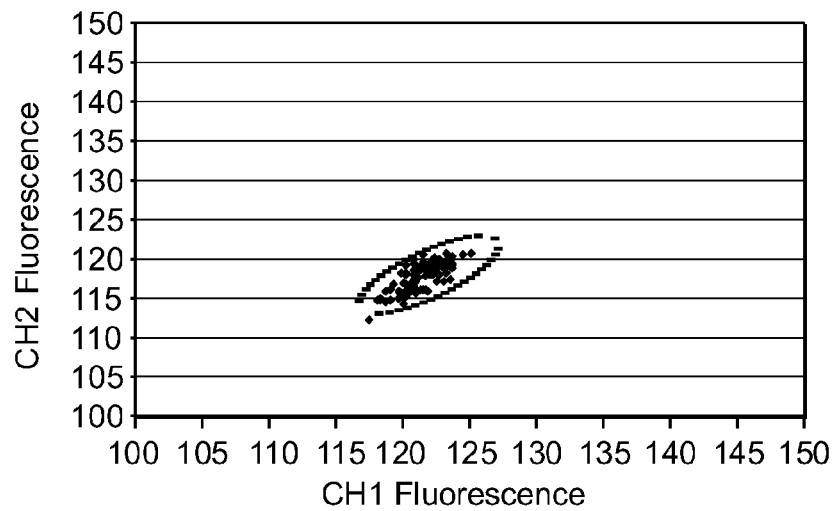
FIG. 5 is a plot illustrating an optimized elliptical, classification region, the original region of FIG. 2, and values for the population of particles.

Finally, the set of points within the ellipse are rotated back to the original dimensions of CH1 and CH2, as shown in FIG. 5, and the resulting ellipse in the original dimensions is the optimized classification region. As further shown in FIG. 5, the optimized classification region has a size that is much smaller than the original classification region.

Figure 6:
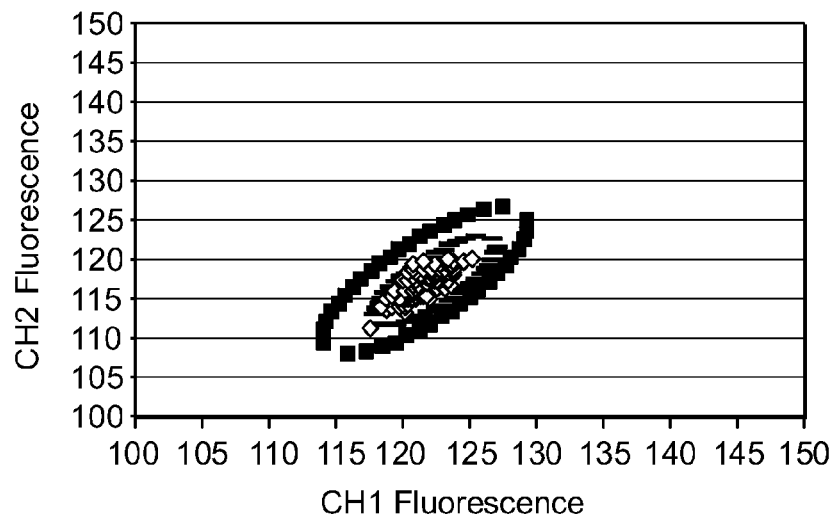
FIG. 6 is a plot illustrating a larger boundary around the optimized classification region of FIG. 5.

Additionally, a larger boundary could be created around the region by generating an ellipse with axes corresponding to a higher number of standard deviations than the classification region. If no other classification regions (for other populations) are placed within this larger boundary, no more than a predetermined percentage of the particles from this region will erroneously be classified in the other region. The converse is also true, given that a similar boundary has also been generated for the other population of particles. In this example, the classification boundary is 3 standard deviations away from the centroid of the population in both axes. The larger boundary might be 5 standard deviations away, which in this case would enclose 100% of the 96 particles in the population. FIG. 6 shows the original region (white area), the population of data points, the first optimized classification region boundary defined by the smaller boundary (smaller ellipse), and the optimized classification region defined by the larger boundary based on 5 standard deviations in both of the rotated coordinate axes (larger ellipse).

Figure 7:
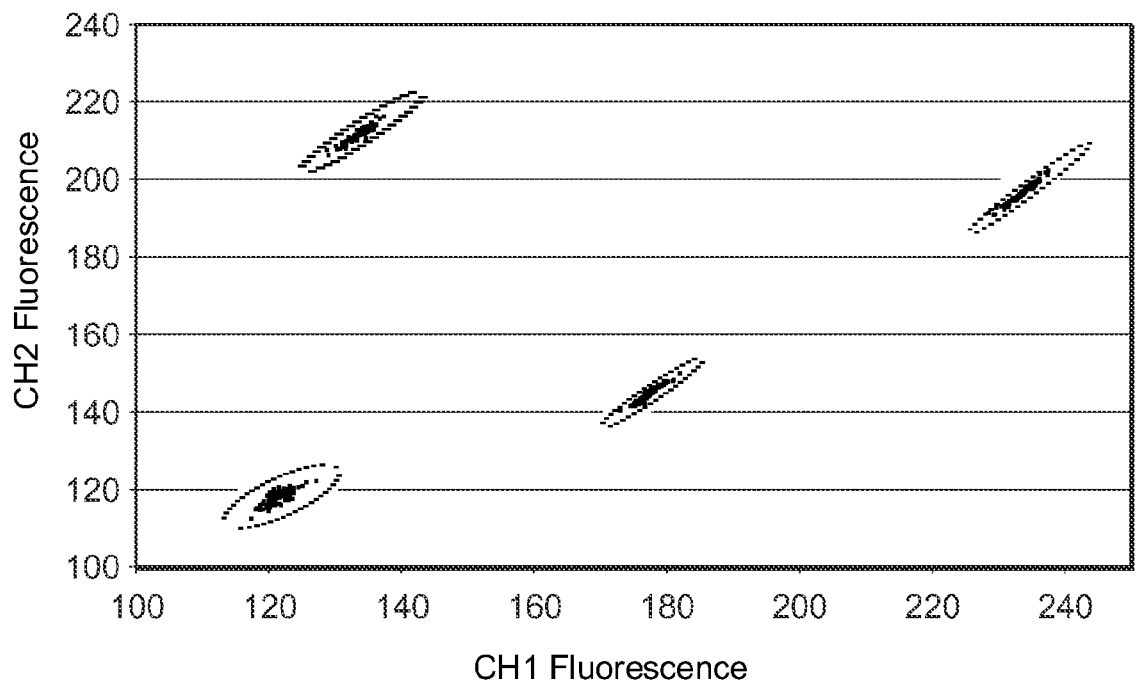
FIG. 7 is a plot illustrating flow cytometer data in a 2-parameter fluorescence plot with four distinct regions, each for different populations of particles.
Figure 8:
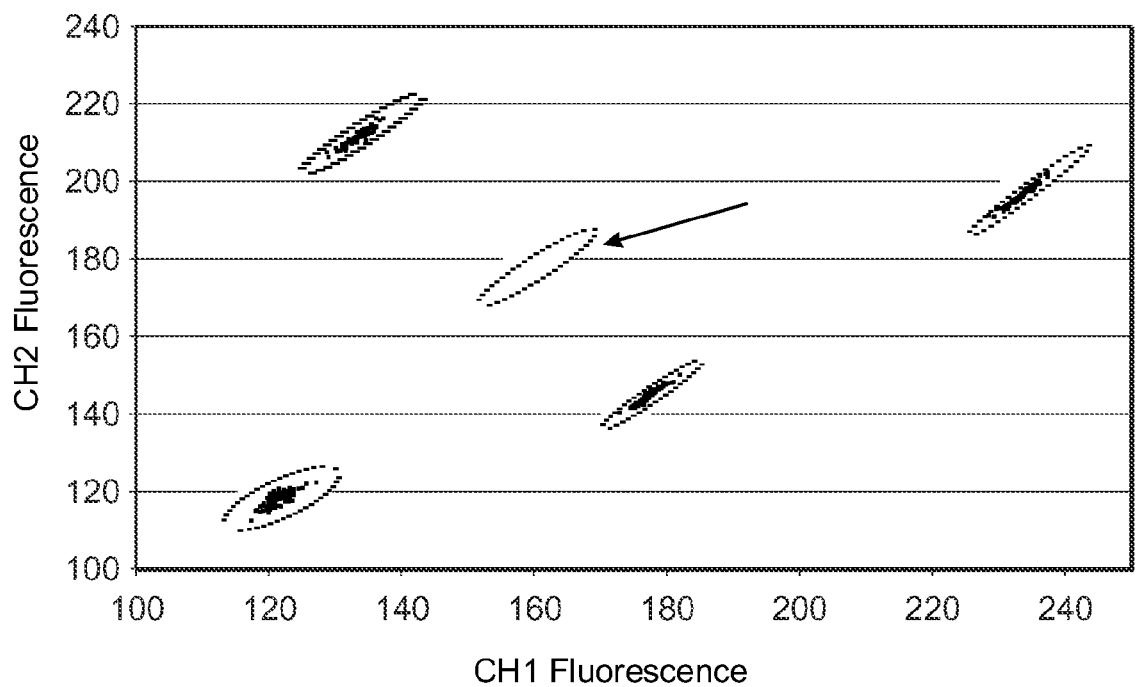
FIG. 8 is a plot illustrating the four original regions of FIG. 7 with a new parametrically generated optimized classification region.

One example of optimizing two or more regions may include the following steps, which may produce data as illustrated in FIGS. 7-8. It is noted that the data illustrated in FIGS. 7-8 is not meant to be exemplary or limiting examples of the methods described herein. Instead, this data is presented merely to enhance understanding of the methods described herein. FIG. 7 shows data generated by a flow cytometer-like device during analysis of a sample containing four different populations of fluorescently-dyed particles. The optimized elliptical regions have been created for each region corresponding to one of the populations as described in the above example, but ellipses with major and minor axes of 5 standard deviations were used so that the optimized classification regions appear distinct from the data points. In practice, smaller classification regions would probably be optimal.

These four optimized classification regions can be used to generate an additional optimized classification region for another population without actually having data for the new population. The parameters used to generate the additional optimized classification region are its location in terms of CH1 and CH2 coordinates. A model is generated from the four optimized classification regions that were created from actual data values generated by analysis of the sample, and input parameters for the model are also region locations in CH1 and CH2 coordinates. Then, the additional optimized classification region can be interpolated anywhere in the CH1-CH2 space without actually having measurement data for the particular optimized classification region being generated.

For the four regions shown in FIG. 7, the region coordinates are shown in Table 1:

TABLE 1

|  | CH1 | CH2 |
| --- | --- | --- |
| Region 1 | 120 | 118 |
| Region 2 | 176 | 145 |
| Region 3 | 232 | 197 |
| Region 4 | 134 | 212 |

These coordinates represent the positions of the centroids of the original classification region (as shown by the white areas in FIG. 7).

Based on the coordinates of the positions of the centroids, the following statistics are calculated for each region:

1. Centroid shift in CH1 (the vector connecting the original region centroid in CH1 and the optimized classification region centroid in CH1);
2. Centroid shift in CH2 (the vector connecting the original region centroid in CH2 and the optimized classification region centroid in CH2);
3. Slope of best-fit line through values for a population;
4. Standard deviations of the values for a population in CH1' and CH2' (rotated) coordinates; and
5. Number of standard deviations required to encircle the desired percentage of values for particles in each population.

A regression model is built to create models for each of these five statistics as functions of the CH1 and CH2 coordinates shown in Table 1. For example, with this data, the form of the expression for statistic 3 was the following equation:

$$\text{Slope}=0.515+(CH1*0.00205)+(CH2*0.00165)$$

Once these five statistics are calculated for any pair of coordinates in CH1 and CH2, an optimized elliptical region can be automatically generated using only that pair of numbers. FIG. 8 shows the original four regions from FIG. 7 plus a fifth optimized elliptical region generated for the original region labeled with the arrow. This process could be repeated multiple times, so that many new optimized regions could be generated using only the data collected from the original four populations, as shown in FIG. 7.

Figure 9:
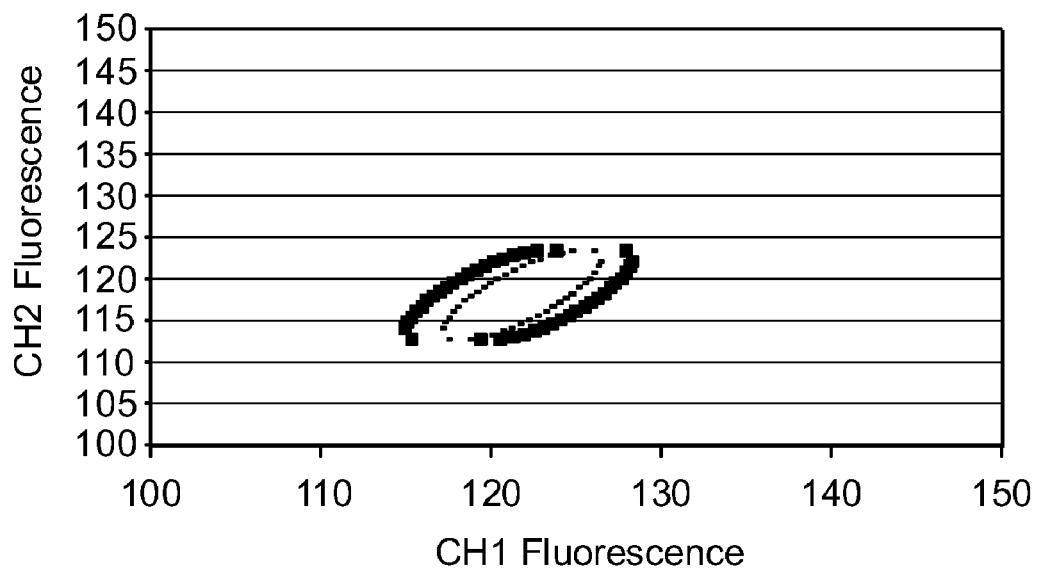
FIG. 9 is a plot illustrating a region enlarged in the CH1 direction.
Figure 10:
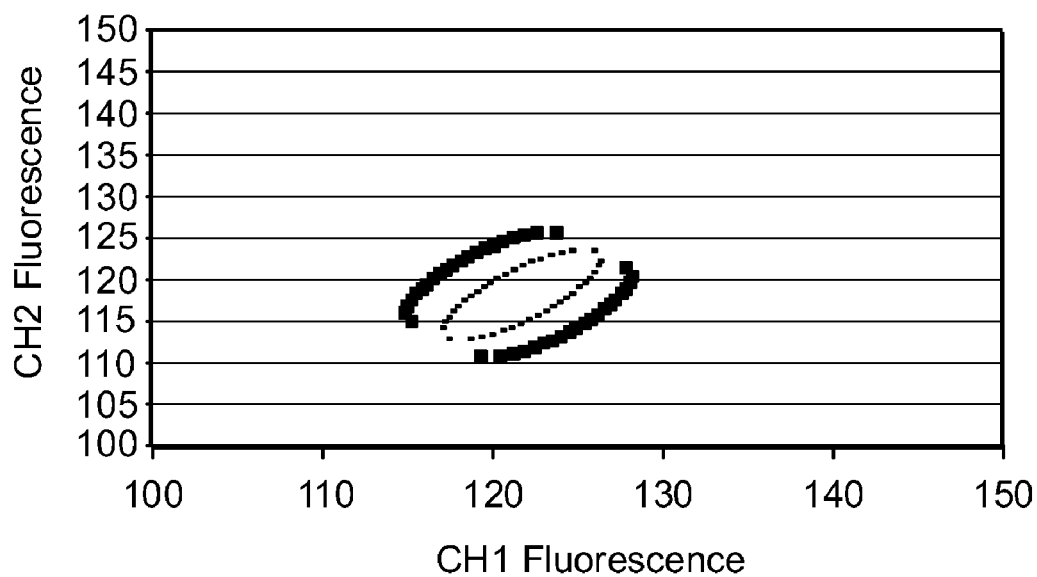
FIG. 10 is a plot illustrating a region enlarged in the CH1 and CH2 directions.

One example of enlarging a particular region to account for extraneous sources of error may include the following steps, which may produce data as illustrated in FIGS. 9-10. It is noted that the data illustrated in FIGS. 9-10 is not meant to be exemplary or limiting examples of the methods described herein. Instead, this data is presented merely to enhance understanding of the methods described herein. Experience indicates that other sources of error, such as aged calibration reagents, might increase the size of the boundary that captures the desired percentage of particles in each region (which may be performed as described in the above examples). If it is known that the centroid of a particular region may deviate by a certain number of units based on these sources of error, then the region may be widened by that amount. In the example of determining an optimized classification region described above, if the user wants to allow for a shift of 2 counts in either direction for the CH1 axis, then the boundary to the right and left of the region's centroid in the CH1 direction can both be shifted away from the centroid by that amount (as shown in FIG. 9). Similarly, the method could be applied to the CH2 direction, or to both directions for the same region (as shown in FIG. 10).

Figure 11:
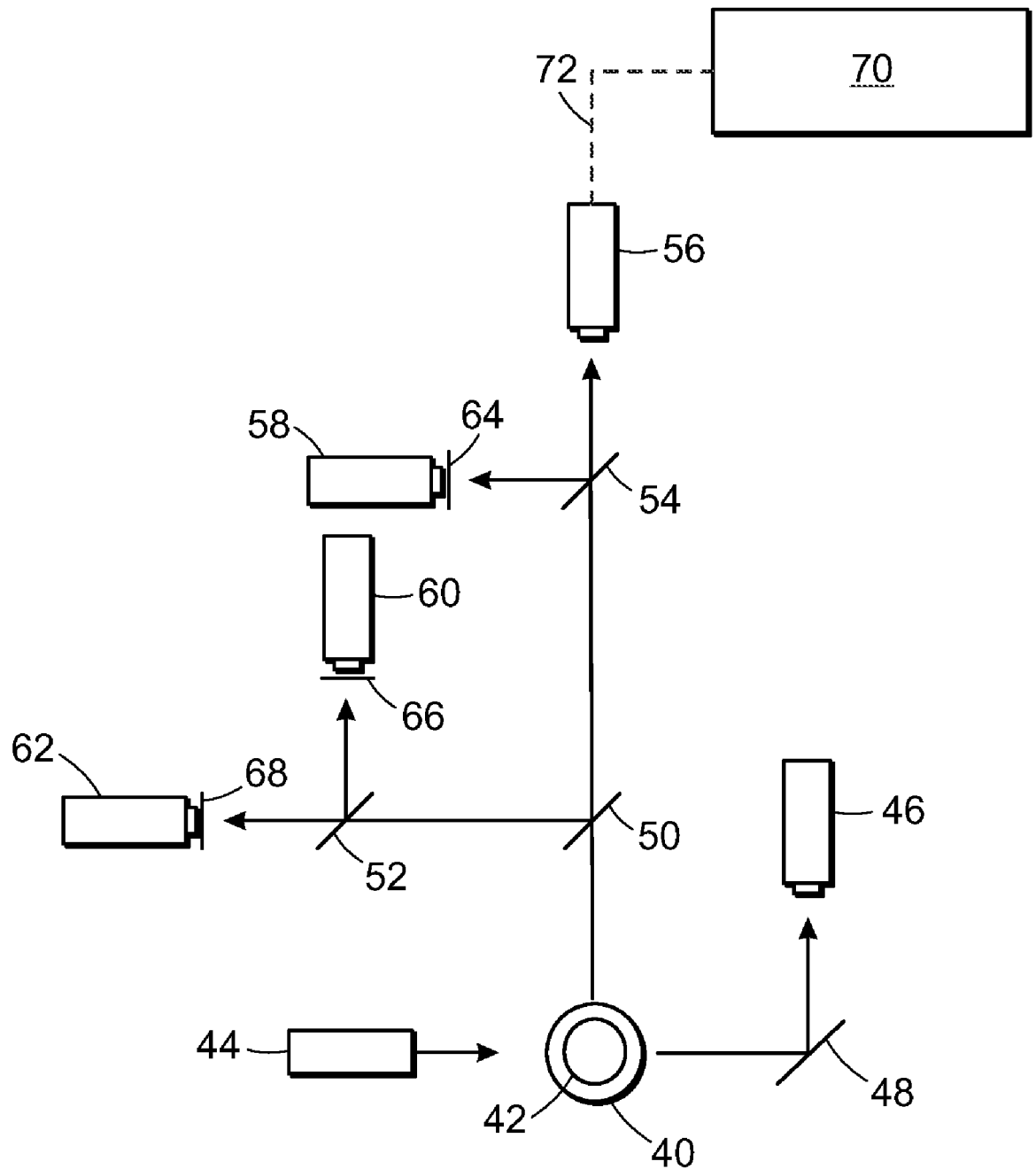
FIG. 11 is a schematic diagram illustrating one example of a flow cytometer-based measurement system that may be used to carry out the methods described herein.

FIG. 11 illustrates one example of a measurement system that may be used to perform the methods described herein. It is noted that FIG. 11 is not drawn to scale. In particular, the scale of some of the elements of the figure are greatly exaggerated to emphasize characteristics of the elements. Some elements of the measurement system have not been included in the figure for the sake of clarity.

In FIG. 11, the measurement system is shown along a plane through the cross-section of cuvette 40 through which microspheres 42 flow. In one example, the cuvette may be a standard quartz cuvette such as that used in standard flow cytometers. Any other suitable type of viewing or delivery chamber, however, may also be used to deliver the sample for analysis. The measurement system includes light source 44. Light source 44 may include any appropriate light source known in the art such as a laser. The light source may be configured to emit light having one or more wavelengths such as blue light or green light. Light source 44 may be configured to illuminate the microspheres as they flow through the cuvette. The illumination may cause the microspheres to emit fluorescent light having one or more wavelengths or wavelength bands. In some embodiments, the system may include one or more lenses (not shown) configured to focus light from the light source onto the microspheres or the flowpath. The system may also include more than one light source. In one embodiment, the light sources may be configured to illuminate the microspheres with light having different wavelengths or wavelength bands (e.g., blue light and green light). In some embodiments, the light sources may be configured to illuminate the microspheres at different directions.

Light scattered forwardly from the microspheres may be directed to detection system 46 by folding mirror 48 or another such light directing component. Alternatively, detection system 46 may be placed directly in the path of the forwardly scattered light. In this manner, the folding mirror or other light directing components may not be included in the system. In one embodiment, the forwardly scattered light may be light scattered by the microspheres at an angle of about 180 degrees from the direction of illumination by light source 44, as shown in FIG. 11. The angle of the forwardly scattered light may not be exactly 180 degrees from the direction of illumination such that incident light from the light source may not impinge upon the photosensitive surface of the detection system. For example, the forwardly scattered light may be light scattered by the microspheres at angles less than or greater than 180 degrees from the direction of illumination (e.g., light scattered at an angle of about 170 degrees, about 175 degrees, about 185 degrees, or about 190 degrees).

Light scattered by the microspheres at an angle of about 90 degrees from the direction of illumination may also be collected. In one embodiment, this scattered light may be separated into more than one beam of light by one or more beamsplitters or dichroic mirrors. For example, light scattered at an angle of about 90 degrees to the direction of illumination may be separated into two different beams of light by beamsplitter 50. The two different beams of light may be separated again by beamsplitters 52 and 54 to produce four different beams of light. Each of the beams of light may be directed to a different detection system, which may include one or more detectors. For example, one of the four beams of light may be directed to detection system 56. Detection system 56 may be configured to detect light scattered by the microspheres.

Scattered light detected by detection system 46 and/or detection system 56 may generally be proportional to the volume of the particles that are illuminated by the light source. Therefore, output signals of detection system 46 and/or output signals of detection system 46 may be used to determine a diameter and/or volume of the particles that are in the illumination zone or detection window. In addition, the output signals of detection system 46 and/or detection system 56 may be used to identify more than one particle that are stuck together or that are passing through the illumination zone at approximately the same time. Therefore, such particles may be distinguished from other sample microspheres and calibration microspheres. Furthermore, the output signals of detection system 46 and/or detection system 56 may be used to distinguish between sample microspheres and calibration microspheres.

The other three beams of light may be directed to detection systems 58, 60, and 62. Detection systems 58, 60, and 62 may be configured to detect fluorescence emitted by the microspheres. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence.

In some embodiments, spectral filters 64, 66, and 68 may be coupled to detection systems 58, 60, and 62, respectively. The spectral filters may be configured to block fluorescence of wavelengths other than that which the detection systems are configured to detect. In addition, one or more lenses (not shown) may be optically coupled to each of the detection systems. The lenses may be configured to focus the scattered light or emitted fluorescence onto a photosensitive surface of the detectors.

Each of the detector's output currents is proportional to the fluorescent light impinging on it and results in a current pulse. The current pulse may be converted to a voltage pulse, low pass filtered, and then digitized by an A/D converter. The conversion, filtering, and digitizing may be performed using any suitable components known in the art. The measurement system may also include processor 70. Processor 70 may be coupled to the detectors by one or more transmission media and optionally one or more components interposed between the processor and the detectors. For example, processor 70 may be coupled to detection system 56 by transmission medium 72. The transmission medium may include any suitable transmission medium known in the art and may include "wired" and "wireless" portions. The processor may include, in one example, a DSP that is configured to integrate the area under the pulse to provide a number which represents the magnitude of the fluorescence. The processor may also be configured to perform one or more of the steps of the embodiments described herein.

In some embodiments, the output signals generated from fluorescence emitted by the microspheres may be used to determine an identity of the microspheres and information about a reaction taking place on the surface of the microspheres. For example, output signals of two of the detection systems may be used to determine an identity of the microspheres, and output signals of the other detection system may be used to determine a reaction taking place on the surface of the microspheres. Therefore, the selection of the detectors and the spectral filters may vary depending on the type of dyes incorporated into or bound to the microspheres and/or the reaction being measured (i.e., the dye(s) incorporated into or bound to the reactants involved in the reaction).

The values generated by detections systems 46, 56, 58, 60, and 62 may be used in the methods described herein. In one particular example, the values generated by two of the detection systems for a microsphere may be compared, in a classification space, to one or more optimized classification regions, which are determined as described above. The classification of the microsphere may be determined as the classification assigned to the optimized classification region in which the values are located.

The detection systems that are used to determine an identity of the sample microspheres (e.g., detection systems 58 and 60) may be avalanche photodiodes (APDs), a photomultiplier tube (PMT), or another photodetector. The detection system that is used to identify a reaction taking place of the surface of the microspheres (e.g., detection system 62) may be a PMT, an APD, or another form of photodetector.

Although the system of FIG. 11 is shown to include two detection systems having two different detection windows for distinguishing between microspheres having different dye characteristics, it is to be understood that the system may include more than two such detection windows (i.e., 3 detection windows, 4 detection windows, etc.). In such embodiments, the system may include additional beamsplitters and additional detection systems having other detection windows. In addition, spectral filters and/or lenses may be coupled to each of the additional detection systems. In another embodiment, the system may include two or more detection systems configured to distinguish between different materials that are reacted on the surface of the microspheres. The different reactant materials may have dye characteristics that are different than the dye characteristics of the microspheres.

Additional examples of measurement systems that may be used to perform the methods described herein are illustrated in U.S. Pat. No. 5,981,180 to Chandler et al., U.S. Pat. No. 6,046,807 to Chandler, U.S. Pat. No. 6,139,800 to Chandler, U.S. Pat. No. 6,366,354 to Chandler, U.S. Pat. No. 6,411,904 to Chandler, U.S. Pat. No. 6,449,562 to Chandler et al., and U.S. Pat. No. 6,524,793 to Chandler et al., which are incorporated by reference as if fully set forth herein. The measurement system described herein may also be further configured as described in these patents.

Program instructions implementing methods such as those described herein may be transmitted over or stored on a carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, a processor may be configured to execute the program instructions to perform a computer-implemented method according to the above embodiments. The processor may take various forms, including a personal computer system, mainframe computer system, workstation, network appliance, Internet appliance, personal digital assistant ("PDA"), television system or other device. In general, the term "computer system" may be broadly defined to encompass any device having one or more processors, which executes instructions from a memory medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

It will be appreciated to those skilled in the art having the benefit of this disclosure that this invention is believed to provide methods for altering one or more parameters of a measurement system. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for altering one or more parameters of a measurement system, comprising:

analyzing a sample using the system to generate values from classification channels of the system for two or more populations of particles in the sample;

identifying two or more regions in a classification space, wherein in each of the two or more regions the values for one of the two or more populations of particles are located;

determining two or more optimized classification regions, wherein each of the two or more optimized classification regions corresponds to one of the two or more regions; and interpolating an optimized classification region for an additional population of particles not included in the sample using the two or more optimized classification regions.

2. The method of claim 1, wherein the step of interpolating the optimized classification region for the additional population of particles comprises interpolating optimized classification regions for a plurality of different populations of particles not included in the sample using the two of more optimized classification regions.

3. The method of claim 1, wherein the step of interpolating the optimized classification region for the additional population of particles comprises:

calculating one or more statistics for each of the two or more optimized classification regions;

creating a regression model for each of one or more statistics as a function of centroid coordinates of the two or more optimized classification regions;

inputting different centroid coordinates associated with the additional population of particles into the regression model to compute one or more statistics for the optimized classification region for the additional population of particles; and generating the optimized classification region for the additional population of particles based on said computed statistics.

4. A method for altering one or more parameters of a measurement system, comprising:

analyzing a sample using the system to generate values from classification channels of the system for a population of particles in the sample;

identifying a region in a classification space in which the values for the population are located, wherein the identified region is one of a plurality of distinct and preassigned regions within the classification space; and subsequently determining an optimized classification region for the population using one or more properties of the values of the population, wherein the optimized classification region comprises a first portion of the identified region and excludes a second portion of the identified region, wherein a probability that the particles will have values located in the first portion of the identified region is greater than a predetermined probability, and wherein the optimized classification region is used for classification of particles in additional samples.

5. The method of claim 4, wherein the optimized classification region has one or more properties that are different from one or more respective properties of the identified region, and wherein the one or more properties comprise size, shape, position, or some combination thereof.

6. The method of claim 4, wherein the one or more properties of the values of the population comprise an average, mean, peak, or median of the values of the population and a standard deviation of the values of the population.

7. The method of claim 4, wherein the optimized classification region centers on a median of the values for the population plus a number of standard deviations away from the median.

8. The method of claim 4, wherein the optimized classification region is defined by a predetermined sized boundary surrounding a median of the values for the population.

9. The method of claim 4, wherein the sample comprises one or more additional populations of particles, the method further comprising performing the method for the one or more additional populations.

10. The method of claim 4, wherein the sample comprises one or more additional populations of particles, the method further comprising performing the method for the one or more additional populations and interpolating an optimized classification region for another population of particles that was not included in the sample using the optimized classification regions of the population and the one or more additional populations.

11. The method of claim 4, wherein the one or more properties of the values of the population comprise an average, mean, peak, or median of the values of the population and a standard deviation of the values of the population, the method further comprising comparing at least one of the one or more properties of the values of the population to a predetermined range for the at least one of the one or more properties of the values of the population.

12. The method of claim 11, further comprising assessing performance of the system based on results of said comparing.

13. The method of claim 11, further comprising determining if one or more corrective steps should be performed on the system upon detecting the at least one of the one or more properties is outside of the predetermined range.

14. The method of claim 4, further comprising comparing one or more properties of the optimized classification region to the one or more properties of the identified region.

15. The method of claim 14, wherein the one or more properties of the optimized classification region and the identified region comprise size, centroid position, slope of a best-fit line to the values inside the identified region or the optimized classification region, offset of the best-fit line, or some combination thereof.

16. The method of claim 14, further comprising determining if the system is malfunctioning upon detecting one or more properties of the optimized classification region exceed one or more respective properties of the identified region.

17. A method for altering one or more parameters of a measurement system, comprising:
identifying a region in a classification space in which values for a population of particles of a sample correspond, wherein the values comprise values generated by classification channels of the system during analysis of the sample; and
determining an optimized classification region for the population using one or more properties of the values of the population, wherein the optimized classification region is used for classification of particles in additional samples, and wherein the program instructions for determining the optimized classification region comprise program instructions for:
creating a provisional region comprising:
a center that is statistically representative of the values for the population; and
one or more dimensions which are characterized by a first predetermined constant multiplied by standard deviations of the values for the population;
determining a percentage of particles arranged within the provisional region; and
performing one or more responsive actions based upon the step of determining the percentage of particles, wherein the responsive actions comprise:
assigning the provisional region as the optimized classification region upon determining the percentage of particles is greater than or equal to the preset percentage;
adjusting the one or more dimensions of the provisional region upon determining the percentage of particles is less than the preset percentage, wherein the step of adjusting the one or more dimensions comprises multiplying the standard deviations of the values for the population by a different predetermined constant; and
reiterating the steps of determining the percentage of particles and performing the one or more responsive actions subsequent to the step of adjusting the axes until a provisional region is formed having a percentage of the particles greater than or equal to the predetermined percentage.

18. The method of claim 17, further comprising comparing one or more properties of the optimized classification region to the one or more properties of the identified region.

19. The method of claim 18, further comprising assessing performance of the system based on results of said comparing.

20. The method of claim 18, further comprising determining if the system is malfunctioning upon detecting one or more properties of the optimized classification region exceed one or more respective properties of the identified region.

* * * * *